US006673727B2

(12) United States Patent
Morris et al.

(10) Patent No.: US 6,673,727 B2
(45) Date of Patent: Jan. 6, 2004

(54) ORTHOPEDIC CASTS WITH CONTROLLED FLEXIBILITY

(75) Inventors: Roy A. Morris, Plantation, FL (US); Jose A. Alvarez, San Juan, PR (US)

(73) Assignee: EBI, L.P., Parsippany, NJ (US)

( * ) Notice: Subject to any disclaimer, the term of this patent is extended or adjusted under 35 U.S.C. 154(b) by 292 days.

(21) Appl. No.: 09/775,297

(22) Filed: Feb. 1, 2001

(65) Prior Publication Data

US 2002/0160684 A1 Oct. 31, 2002

(51) Int. Cl.$^7$ ................................................ B32B 27/04
(52) U.S. Cl. .................... 442/105; 442/169; 442/171; 442/175; 442/180; 442/415; 442/416; 602/8; 523/111
(58) Field of Search ................................ 442/180, 415, 442/416, 105, 169, 171, 175; 602/8; 523/111

(56) References Cited

U.S. PATENT DOCUMENTS

| | | | |
|---|---|---|---|
| 3,373,741 A | 3/1968 | Hill et al. ...................... 602/8 |
| 3,847,722 A | 11/1974 | Kistner ......................... 428/76 |
| 4,131,114 A | 12/1978 | Kirkpatrick et al. ........... 602/8 |
| 4,376,438 A | 3/1983 | Straube et al. .................. 602/8 |
| 4,411,262 A | 10/1983 | von Bonin et al. .............. 602/8 |
| 4,427,003 A | 1/1984 | Fennimore et al. ............. 602/8 |
| 4,433,680 A | 2/1984 | Yoon ............................... 602/8 |
| 4,442,833 A | 4/1984 | Dahlen et al. .................. 602/8 |
| 4,473,671 A | 9/1984 | Green ........................... 523/105 |
| 4,502,479 A | 3/1985 | Garwood et al. ............... 602/8 |
| 4,519,856 A | 5/1985 | Lazzara ........................ 156/49 |
| 4,609,578 A | 9/1986 | Reed ............................. 428/76 |
| 4,655,208 A | 4/1987 | Yoon ............................... 602/8 |
| 4,667,661 A | 5/1987 | Scholz et al. ................... 602/8 |
| 4,690,842 A | 9/1987 | Kammerer et al. ...... 206/524.1 |
| 4,705,840 A | 11/1987 | Buckanin ....................... 528/53 |
| 4,745,912 A | 5/1988 | McMurray ...................... 602/8 |
| 4,774,937 A | 10/1988 | Scholz et al. ................... 602/8 |
| 4,893,617 A | 1/1990 | Bartial et al. ................... 602/8 |
| 4,937,146 A | 6/1990 | Dull et al. ................ 428/423.1 |
| 4,968,542 A | 11/1990 | Gasper et al. ................. 428/76 |
| 5,438,709 A | 8/1995 | Green et al. ..................... 2/167 |
| 5,439,439 A | 8/1995 | Green et al. ..................... 602/6 |
| 5,476,440 A | 12/1995 | Edenbaum ...................... 602/8 |
| 5,512,354 A | 4/1996 | Scholz et al. ................ 442/306 |
| 5,738,639 A | 4/1998 | Cueman et al. ................. 602/6 |
| 5,800,899 A | 9/1998 | Sandvig et al. ............... 428/96 |
| 5,913,840 A | 6/1999 | Allenberg et al. .............. 602/8 |
| 5,925,004 A | 7/1999 | Doubleday et al. ............. 602/6 |
| 5,984,884 A | 11/1999 | Alvarez et al. ................. 602/6 |

FOREIGN PATENT DOCUMENTS

| | | |
|---|---|---|
| EP | 0522826 A1 | 7/1992 |
| EP | 0708851 B1 | 7/1994 |
| EP | 0712618 A2 | 11/1995 |
| GB | 1578895 | 11/1980 |
| JP | 54-100181 | 8/1979 |
| WO | WO94/23769 | 10/1994 |
| WO | WO95/04178 | 2/1995 |
| WO | WO96/39201 | 12/1996 |
| WO | WO 99/65433 | 12/1999 |
| WO | WO 02/060499 | 8/2002 |

OTHER PUBLICATIONS

International Preliminary Examination Report; International App. No. PCT/US02/03137, International Filing Date Jan. 31, 2002.

International Search Report or The Declaration; International App. No. PCT/US02/03137; International Filing Date Jan. 31, 2002.

*Primary Examiner*—Terrel Morris
*Assistant Examiner*—John J. Guarriello
(74) *Attorney, Agent, or Firm*—Harness, Dickey & Pierce, P.L.C.

(57) ABSTRACT

An orthopedic casting material comprising a substrate impregnated with a water-curable resin comprising an aromatic polyisocyanate and a polyol, wherein the free NCO level of said prepolymer is from about 6% to about 10%. Preferably the free NCO level is from about 7% to about 8%. Preferably the polyol has a molecular weight of at least 2,000, and a hydroxyl number of from about 28 to about 56, preferably from about 35 to about 40. The casting material may be packaged as a kit with a casting aid comprising a substrate impregnated with a lubricating material.

42 Claims, No Drawings

ORTHOPEDIC CASTS WITH CONTROLLED FLEXIBILITY

BACKGROUND OF THE INVENTION

The present invention relates to novel materials for making orthopedic casts. In particular, this invention relates to urethane resin systems useful in making orthopedic casts that have levels of flexibility that can be controlled depending on specific therapeutic needs.

A variety of materials are known in the art for protecting or immobilizing arms, legs, or other body members. Casts and splints are used, for example, to protect a body part from injury, or to allow a broken bone to heal properly. Historically, such casts were made of plaster of paris. However, plaster casts have recently been largely replaced in many applications by orthopedic bandages or sheets impregnated with synthetic resin mixtures. The synthetic resins used in combination with certain knitted or woven substrates offer a number of advantages over the old plaster materials. In particular, casts made from the synthetic materials are lighter, stronger, harden more quickly, allow for better air circulation, and are not water sensitive.

Among the synthetic resin compositions used to prepare casting materials are water-activated or water-curable synthetic resin compositions, and thermoplastic resin compositions. The water-activated or water-curable synthetic resin is impregnated auto bandages or sheets, which are typically referred to as "tapes". As with old plaster casting materials, these resin-impregnated sheets are wetted before application to the body member. The water begins the curing reaction that hardens the cast. Other compositions for casting materials use synthetic resin compositions employing different kinds of curing mechanisms, for example crosslinking through unsaturation.

Particularly preferred synthetic resins for orthopedic casts are the polyurethanes. Such resin systems comprise a water-curable mixture of an isocyanate and a hydroxy-containing compound. Casts made with such materials are disclosed in, for example, Japanese Patent Publication 54-100181, Takazawa et al., published Aug. 7, 1979; British Patent Specification 1,578,895, Straube et al., published Nov. 12, 1980; U.S. Pat. No. 4,131,114, Kirkpatrick et al., issued Dec. 26, 1978; U.S. Pat. No. 4,376,438, Straube et al., issued Mar. 15, 1983; U.S. Pat. No. 4,411,262, von Bonin, et al., issued Oct. 25, 1983, issued Feb. 28, 1984; U.S. Pat. No. 4,433,680, Yoon, issued Feb. 28, 1984; U.S. Pat. No. 4,473,671, Green, issued Sep. 25, 1984; U.S. Pat. No. 4,502,479, Garwood et al., issued Mar. 5, 1986; U.S. Pat. No. 4,609,578, Reed, issued Sep. 2, 1986; U.S. Pat. No. 4,667,661, Scholz et al., issued May 26, 1987; U.S. Pat. No. 4,774,937, Scholz et al., issued Oct. 4, 1988 and U.S. Pat. No. 4,968,542, Gasper et al., issued Nov. 6, 1990.

Such casts are typically rigid when cured, with no flexibility. As with plaster casts, such rigid urethane casts may be useful in therapeutic applications where total immobilization is desired. Non-rigid casts are also known in the art, for use in applications where some degree of movement is permissible or desired. The use of such casts for prevention of injuries (e.g., sports injuries) is described in U.S. Pat. No. 4,968,542, Gasper et al. However non-rigid casts among those known in the art may be too soft for many applications, and afford a limited range of uses unless combined with more rigid materials during the cast formation process. Moreover, such casts may also have limited durability during use, resulting in delamination where layers of the cast separate, compromising the structural integrity of the cast.

SUMMARY OF THE INVENTION

The present invention provides improved casting materials that have an optimal degree of flexibility relative to rigid and semi-rigid casting materials known in the art. Preferred compositions of this invention comprise a substrate impregnated with a water-curable resin comprising an aromatic polyisocyanate and a polyol, wherein the free NCO level of said resin is from about 6% to about 10%. Preferably the free NCO level is from about 7% to about 10%, more preferably from about 7% to about 8%.

Applicants have found that the methods and articles of this invention provide benefits versus casting compositions among those in the art. Such benefits, including enhanced ability to be used in a variety of therapeutic and preventative applications, improved usage characteristics, and improved stability of casts made using the compositions.

DETAILED DESCRIPTION

The invention provides compositions that are used to make orthopedic casts. As referred to herein, an "orthopedic cast" is a device that encloses, in whole or in part, a body member (e.g., a leg) of a human or other animal subject. Such casts may be used for the prevention of injury, or in the treatment of disorders such as broken bones. Specific compounds, compositions and other components to be used in such orthopedic casts must, accordingly, be pharmaceutically and cosmetically acceptable. As used herein, such a "pharmaceutically and cosmetically acceptable" component is one that is suitable for use with humans and/or animals without undue adverse side effects (such as toxicity, irritation, and allergic response) commensurate with a reasonable benefit/risk ratio.

Curable Resin:

The compositions of this invention comprise a water-curable resin. As referred to herein, a "water-curable resin" is a polyurethane prepolymer that is curable upon contact with water. Such contact may be to water vapor (e.g., through exposure to air), through immersion of the composition in water, or through any other means which effects sufficient exposure of the composition to water so as to initiate curing of the resin.

Curable resins of this invention comprise, and may be prepared by reacting, one or more polyisocyanates and one or more polyols. The polyisocyanate may be aliphatic, cycloaliphatic, or aromatic diisocyanates, triisocyanates, or tetraisocyanates, as well as biurets, isocyanurates, and similar oligomers of these. Examples of useful polyisocyanates include, without limitation, toluene diisocyanates (TDI), including the 2,4 and 2,6 isomers and mixtures of these isomers; diphenyhnethane diisocyanates (MDI), including the 4,4', 2,4', and 2,2' isomers and mixtures of these isomers; hydrogenated diphenylmethane diisocyanates, aromatic polyisocyanates derived from phosgenation of the condensation product of aniline and formaldehyde (polymeric MDI), hexamethylene diisocyanate, isophorone diisocyanate, octamethylene diisocyanate, trimethylhexane diisocyanates, dodecamethylene diisocyanates, cyclopentane diisocyanate, cyclohexane diisocyanate, tetramethylxylene diisocyanate, and biurets, allophonates, isocyanurates, and substituted derivatives of these, such as carbodiimide-containing polyisocyanates. (As used herein, the words "include" and "including" are intended to be non-limiting, such that items that are included in a list are not to the exclusion of other like items that may be useful in the compositions and methods of this invention.) Preferred isocyanates include polymeric diphenylmethane diisocyanates (polymeric MDI's).

The polyisocyanate is reacted with at least one polyol. Examples of suitable polyols include, without limitation, polyether polyols, polyester polyols including polycaprolactone polyols, and monomeric diols and triols such as 1,6-hexanediol. Preferred polyols include polyethylene oxide and polypropylene oxide diols and triols, having a molecular weight of at least about 2,000, preferably from about 2,000 to about 4,000, more preferably from about 3,000 to about 4,000. Preferably the polyol has a hydroxyl number of from about 28 to about 56, preferably from about 28 to about 46, more preferably from about 35 to about 40. As referred to herein, the "hydroxyl number" is the number of milligrams, per gram of polyol, of potassium hydroxide having an acid neutralization capacity equal to the polyol. Preferred polyols include PPG 3025, having a molecular weight of about 3,000 and a hydroxyl number of from about 35 to about 40, sold by Lyondell Chemical Company, and QO Polymeg 3000, having a molecular weight of from about 2,800 to about 3,000 and a hydroxyl number of from about 37 to about 40, sold by Great Lakes Chemical Corporation.

The curable resins of this invention have a level of free NCO of from about 6% to about 10%, preferably from about 7% to about 10%, preferably from about 7% to about 8%, more preferably about 7.5%. As referred to herein, the "level of free NCO" is the weight of the equivalents of NCO in excess of the equivalents of polyol in the prepolymer, as a percentage of the total weight of the prepolymer (weight of isocyanate plus the weight of the polyol). An example of the calculation of free NCO is set forth in Example 1, below.

The compositions of this invention preferably contain a catalyst. Preferred catalysts include tertiary amine catalysts such as tertiary alkanolamines, for example dimethylethanolamine and dimethylaminodiethyl ether; 2,2'-dimorpholinodialkylethers such as 2,2'-dimorpholinodiethylether (DMDEE), available commercially from Texaco, Inc., as Thancat DMDEE; and 2,2'-dimorpholinyldialkylethers, such as 4-[2-[methyl-2-(4-morpholinyl)ethoxy]-ethyl]morpholine (MEMPE). The catalyst is preferably included in amounts of from about 0.1% to about 10% by weight of the composition.

Preferably the casting material is substantially free of lubricating materials. As used herein, such "lubricating materials" are those disclosed in the art for admixture with the resin so as to make the resin slippery. Such lubricating materials are disclosed, for example, in U.S. Pat. No. 4,667,661, Scholz et al., issued May 26, 1997, and U.S. Pat. No. 4,774,937, Scholz et al., issued Oct. 4, 1988, incorporated by reference herein. As referred to herein, casting materials that are "substantially free" of lubricating materials have no lubricating materials, or levels of lubricating materials that are sufficiently low so as to provide insignificant reduction in the tackiness of the resin. Preferably the casting materials contain less than 1% of such lubricating materials.

The curable resin mixture preferably has a viscosity that is low enough to allow the mixture to enter the pores of the tape, while the viscosity is high enough that a sufficient amount remains in the tape so that, upon curing, the tape is effectively hardened and the desired physical properties are obtained. The viscosity may be modified according to a variety of obvious means, such as by addition of low viscosity materials including, without limitation, organic solvents to reduce viscosity or by addition of thickening agents to increase viscosity. The optimum viscosity may be determined by straightforward testing. In a preferred embodiment of the invention, the viscosity of the curable resin mixture is from about 5000 to about 100,000 centipoise. The impregnating resin mixture may include other ingredients, such as stabilizers, thickening agents, antifoam agents, pigments, and colorants.

The compositions of this invention also comprise a substrate onto which the prepolymer is impregnated. As referred to herein, "impregnated" is the application of the prepolymer to the substrate in a manner which allows the substrate to reach a desired degree of rigidity upon curing of the resin. Such application may be, for example, by coating of the resin on the surface of the substrate, or deposition of the resin into pores or interstitial spaces within the substrate.

The tape, when impregnated with the curable resin, preferably has sufficient flexibility so that it can be molded about a limb without excessive pressure. The casting material is at least partially impregnated with a curable resin. Preferably, the resin mixture may flow into the capillary spaces between fibers of the fabric. Also preferably, the curable resin mixture that is impregnated into the tape comprises from about 25% to about 60%, preferably from about 30% to about 50%, preferably from about 35% to about 48%, more preferably from about 40% to about 45%, by weight of the impregnated tape.

The substrate is preferably is a sheet (herein "casting tape") preferably having an open-weave structure of a fibrous material. Examples of suitable porous material for the casting tape include woven, knit, and non-woven fabrics of natural and/or synthetic fibers. Fabrics among those useful herein are described in U.S. Pat. No. 3,686,725, Nisbet et al., issued Aug. 29, 1972; U.S. Pat. No. 3,787,272, Nisbet et al., issued Jan. 22, 1974; U.S. Pat. No. 4,323,061, Usukura, issued Apr. 16, 1982 U.S. Pat. No. 4,609,578, Reed, issued Feb. 28, 1984; U.S. Pat. No. 4,668,563, Buese et al., issued May 26, 1987, and U.S. Pat. No. 4,745,912, McMurray, issued May 24, 1988; incorporated by reference herein. A preferred embodiment employs a knitted fabric that combines a high modulus fiber, such as a fiberglass, polyaramide, or carbon fiber, with an elastomeric, highly extensible fiber, such as a natural rubber, spandex (a polyurethane), polyisoprene, polybutadiene, diene copolymers, polyalkylene (such as polyethylene or polypropylene), acrylonitrile copolymers, EPM, or EPDM fiber. A particularly preferred tape is comprised of fiberglass and polypropylene, preferably comprising from about 8% to about 18%, more preferably from about 10% to about 14%, of polypropylene.

The tape may be coated with a substance for modifying the fibers of the tape prior to impregnation with the curable resin. The modifying substance preferably does not interfere with the impregnation or detrimentally affect the performance of the curable resin mixture. One example of a modifying substance is a low modulus binder that may be applied to prevent or reduce fraying of cut ends of the substrate, as is disclosed in U.S. Pat. No. 4,800,872, Buese et al., issued Jan. 31, 1989, incorporated by reference herein.

The casting tape is preferably from about 2.7 m (3 yards) to about 4.1 m (4.5 yards), preferably from about 3.6 m (4 yards) to about 3.8 in (4.2 yards) in length and from about 2.5 cm (1 inch) to about 25.4 cm (10 inches), preferably from about 2.5 cm (1 inch) to about 12.7 cm (5 inches), in width. Preferably the casting tape is formed into rolls, and preferably wrapped around a cylindrical core. Preferably the cylindrical core is as described in U.S. Pat. No. 5,984,884, Alvarez et al., issued Nov. 16, 1999 (incorporated by reference herein). Such cylinders preferably have multiple "L"-shaped projections that extend radially outward from the core of the cylinders.

Methods of Use:

The present invention also provides methods for forming an orthopedic cast by hand around a body member of a human or other animal subject, using a casting material comprising a substrate impregnated with a water-curable resin comprising an aromatic polyisocyanate and a polyol, wherein the free NCO level of said prepolymer is from about 6% to about 10%. Orthopedic casts may be used in the prevention or treatment of a variety of disorders, by (for example) application to the foot, ankle, knee, torso, back, neck, hand, or arm of a human or other animal subject. For example, such casts may be used as casts, splints, braces, or protective devices regarding hallux spica, osteotomies, bunionectomies, diabetic foot ulcerations, fractures, segmental disorders, fusions, arthrodosis, skin grafts, tendon injuries, foot-drop, club feet, neuropathic disorders, ankle sprains, Jones fractures, shin splints, congenital hip dislocations, hip luxation, hip dislocations, rib fractures, gastroc ruptures, and functional Collies' fracture treatment. Casts may be formed, for example, as minerva casts, hallux casts, cylinder casts, hinged knee casts, femoral braces, tibia braces, hip spica casts, hyperextension braces, braces for scoliosis treatment, braces for kyphosis treatment, finger splints, short arm casts, scaphoid casts, Bennett's fracture casts, long arm casts, shoulder spica, acromioclavicular and clavicular bandage, velpeau bandage, tracheotomy protection brace, glove spica casts, short arm casts, long arm casts, acromioclavicular and clavicular bandages, functional forearm braces, functional humeral braces, dynamic hand splinting, and static hand splinting.

Methods of this invention generally comprise the steps of:
(1) exposing a casting material of this invention to water;
(2) applying the casting material to a body member; and
(3) allowing the casting material to harden to form an orthopedic cast.

The step of exposing the composition to water comprises any method of contacting the resin with water. Such contact may be to water vapor (e.g., through exposure to air), through immersion of the composition in water, or through any other means which effects sufficient exposure of the composition to water so as to initiate curing of the resin.

The step of applying the casting material to a body member includes methods among those known in the art for applying casting tapes. Typically, such methods using casting tapes comprise wrapping the body member with from 1 to 10 layers, preferably with from 2 to 6 layers, of the casting tape. The number of layers may be varied depending upon the specific body member being wrapped, the intended function of the cast, and the desired rigidity of the cast. In a preferred method, more tape is applied in some areas so as to effect greater rigidity, while less tape is applied in other areas so as to allow flexibility and movement.

Preferably the methods of this invention comprise the use of a glove for applying the casting material, so as to avoid direct contact of the skin with the resinous material. One or two gloves may be used during the methods of this invention. Also preferably, the glove is lubricated so that the resin may be worked with and formed into the cast without sticking to the glove. Gloves may be prelubricated, by coating with a lubricant. Such gloves are disclosed in European Patent Publication 712,618, Richard et al., published May 22, 1988; U.S. Pat. No. 5,438,709, Green et al., issued Aug. 8, 1995; and U.S. Pat. No. 5,439,439, Green et al., issued Aug. 8, 1995; incorporated by reference herein. Lubricants can also be applied to the glove, such as through the use of a mixture of water, sorbitol, mineral oil, and silicone fluid in a commercially product sold by 3M Co., St. Paul, Minn., under the tradename "Cast Cream."

Preferred methods of lubricating gloves comprise the use of a casting aid comprising a substrate coated with a lubricating material. Such preferred methods comprise an additional step of transferring the lubricating material to the glove by contacting a surface of the glove with the casting aid. The additional step is performed prior to the step of applying the casting material, and may be repeated during the step of applying the casting material.

Accordingly, in the step of applying the casting material to a body member, the casting material is wrapped about the subject's body member, or otherwise applied in multiple adjacent layers, using the glove(s) to which the lubricant has been applied by means of the casting aid. The application is assisted by the reduction in tackiness of the substrate relative to the gloves without reducing significantly the tackiness of the cast substrate relative to itself. The casting aid can be picked up and worked between the gloves in order to deposit additional lubricant onto the glove surfaces. When the desired amount of casting material has been wrapped around the body member, it is often desirable to further mold the wrapped cast material about the body member. Lubricating material may be re-applied from the casting aid to the gloves before and during the molding of the wrapped cast material as desired.

Contacting a surface of the glove with the casting aid is performed, for example, by rubbing the casting aid on the desired surface of the glove one or more times. One or both of the casting aid and the glove may be wetted with water or immersed in water before transferring the lubricant to the glove, and this step may be preferred when the lubricant is water soluble or water dispersible. In some cases, the casting aid may be immersed in water or wetted before being used one or more times to deliver lubricant as needed to the gloves.

An important aspect of many of the preferred embodiments of the present invention is the ability of the person applying the casting material to control the amount of lubricant applied to the gloves during molding of the cast, as well as the timing of the application. If the gloves begin to stick to the cast tape during the step of applying the tape, lubricant may be reapplied to the glove(s) by wiping the glove(s) with the casting aid. Accordingly, preferred methods of this invention comprise an additional step of transferring the lubricating material to a surface of the glove performed during the step of applying the casting material to the body member.

It is also sometimes desirable to use less lubricant prior to and during application of the casting material, so that the tape and packaging can be easily handled during the wrapping step. This can be accomplished by limiting the transfer of lubricant from the casting aid to the gloves.

A preferred casting aid is described in U.S. Pat. No. 5,925,004, Doubleday et al., issued Jul. 20, 1999, incorporated by reference herein. Such casting aids comprise a porous substrate impregnated with a lubricating material. The porous substrate preferably has at least some flexibility or deformability that aids in lubricant delivery. It is particularly preferred for the porous substrate to be a film, a foam, or a sponge; or a textile or fabric article, including articles that may be described as cloths, sheets, tapes, towelettes, pads, or the like. In a more preferred embodiment, the porous substrate is a cloth, sheet, towelette, pad, or sponge.

Another preferred casting aid comprises a resin-impermeable substrate, and a lubricating material, wherein said lubricating material is coated on at least one surface of said substrate. As referred to herein, a "resin-impermeable substrate" is a material which is not chemically reactive with, and is substantially impermeable to, the resin with which it is to be used. In embodiments in which the casting aid is packaged with the resinous material, the substrate prevents substantial contact between the resin and the lubricating material which is coated on the substrate.

Preferably, the non-porous substrate has at least some flexibility or deformability that aids in depositing the lubricating material to the glove or other article that is to be lubricated. Preferred substrates include non-porous films. The substrate may have a broad range of sizes, but preferred substrates are of a size that is large enough to deliver a sufficient amount of lubricant but small enough to be easily handled. The substrate is preferably a sheet having a thickness of from about 0.25 mm (1 mil) to about 1.0 mm (4 mil), preferably about 0.5 mm (2 mil). Preferably the substrate sheet is from about 1 cm (0.4 in) to about 50 cm (19.6 in) in length, more preferably from about 3 cm (1.2 in) to about 38 cm (15 in) in length, more preferably from about 5 cm (5.9 in) to about 25 cm (9.8 in) in length. Preferably the substrate sheet is from about 1 cm (0.4 in) to about 50 cm (19.6 in) in width, more preferably from about 2 cm (0.78 in) to about 25 cm (9.8 in) in width, more preferably from about 5 cm (1.9 in) to about 13 cm (5.1 in) in width. The substrate may be an individual sheet, or may be in the form of a continuous web of sheets connected in end-to-end relationship separated by a scored line or perforations, much like paper toweling.

Preferred substrates are made from a thermoplastic polymer, such as polyolefins, polyesters, polymethylpentene, polyetheretherketone, polyvinyl chloride, polyvinylidene fluoride, polycarbonates, acrylics, and acrylic copolymers, nylon, and mixtures thereof. Particularly preferred polymers include polyesters and polyolefins, particularly polyester high and low density polyethylene, and polybutylene. Preferably, polyolefin and polyester films are oxidized using, for example, a high-voltage corona discharge. A preferred substrate comprises polyester, more preferably a Mylar® polyester film, manufactured by E.I. duPont de Nemours and Company. Preferred casting aids comprising such resin impermeable substrates are described in co-filed U.S. paten application Ser. No. 09/775,308, "Casting Aid and Methods of Forming Casts," Morris et al., incorporated by reference herein.

Lubricating materials useful with casting materials comprise a lubricant that can be transferred from the substrate to the glove, and that reduces friction between the glove and the resinous article that is to be formed using the glove. Such lubricating materials preferably do not react with the substrate, glove, or resin used to make the resinous article. Lubricants useful in the lubricating materials include film forming lubricants, preferably film forming) water soluble or hydrophilic polymers. Lubricants useful herein include polyethylene oxide, polyethylene oxide block copolymers such as copolymers of ethylene oxide and propylene oxide, polyvinyl alcohol, hydroxyethyl cellulose, carboxymethyl cellulose, acrylamide-based polymers, and polyvinylpyrrolidone; lecithin-based lubricants; sulfonated or carboxylated polymers, such as sulfonated or carboxylated polyurethanes; hydrophilic, oligomeric diols, such as the reaction product of polyethylene oxide glycol with dimethyl sodium sulfoisophthalate in a 2:1 molar ratio; hydrophobic lubricants and oils, such as mineral oils, petrolatum, vegetable oils, and derivatives thereof; synthetic and natural motor oils; silicones and other fluids, oils, and greases, such as polydimethylsiloxanes, polymethylphenylsiloxanes, and polydiphenylsiloxanes, especially those having viscosities of between about 100 and 100,000 centistokes; fluorinated greases; and mixtures thereof.

Preferred lubricants for use with resin-impermeable substrates include hydrophilic, such as hydroxyethyl cellulose, carboxy methyl cellulose, polyvinyl alcohol, polyvinylpyrrolidone, polyacrylic acid salts, polyethylene oxide homopolymers and copolymers, and mixtures thereof. The lubricating material preferably also comprises a surfactant. Surfactants useful in compositions of the present invention include anionic, nonionic, cationic, zwitterionic and amphoteric surfactants. Surfactants among those useful herein are disclosed in the following documents, all incorporated by reference herein: McCutcheon's, Detergents and Emulsifiers, 1984 Annual, published by Allured Publishing Corporation, Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983; and U.S. Pat. No. 4,275,055, Nachtigal et al., issued Jun. 23, 1981.

A particularly preferred lubricant for use with porous substrates is a mixture of an oil and a surfactant. Silicone oils or mixtures of silicone oils and surfactants are particularly preferred in such lubricants.

The lubricant material may include other ingredients, such as stabilizers, thickening agents, pigments or colorants, dyes, organic solvents and cosolvents. Preferably the lubricating material for use with resin-impermeable substrates contains an antiblocking agent, to facilitate rolling the casting aid by preventing lubricant layers from sticking together. Preferred antiblocking agents include particulates having a particle size of from about 10 microns to about 400 microns, comprising mineral fillers such as talc and calcium carbonate, ceramic microspheres, aluminum or other oxide powders, polymers such as polystyrene, and glass microspheres.

The lubricating material may be coated on the substrate in any fashion that allows the lubricant to be transferred from the substrate to the glove when in use. As used herein, "coated" refers to any process by which lubricant material is deposited on or into the surface of the substrate, preferably resulting in a uniform layer of lubricating material, so that lubricating material may be readily transferred to a glove or hand during use. Preferably, the lubricating material forms an essentially uniform layer covering substantially all of at least one surface of the substrate. In preferred embodiments wherein the substrate is a flexible sheet, the lubricating material can be coated on either or both of the major surfaces of the sheet. Preferably the lubricating material is coated at a level of from about 0.002 to about 0.005 $g/cm^2$. As referred to herein, "$g/cm^2$" is the weight, in grams, of the lubricating material per square centimeter of substrate surface. More preferably, the lubricating material is coated at a level of from about 0.003 to about 0.004 $g/cm^2$.

The casting aid may be packaged, with one or more article per package or container, for storage before use. The invention further provides a container comprising one or more of the casting aids. In the case of a volatile lubricant, the container preferably comprises a closed or, preferably, sealed package capable of preventing evaporation of the lubricating material, wherein the package contains one or more of the casting aids.

Suitable packaging is well known in the art. For example, a package dispenser for dispensing sheets of the invention may comprise a container having a cavity containing a plurality of the sheets. The container may have an opening on one end through which said sheets may be taken or pulled. The container may have one or more leak-proof layers, such as a hermetic seal. The seal may be made of a flexible material or of a deformable plastic coated foil or uncoated foil. The container may be made of either a rigid or a flexible material, or a combination of rigid and flexible materials. For example, the container may be formed from a rigid plastic or semi-rigid plastic such as a polyethylene, polypropylene, polyethylene terephthalate, or from a more flexible material such as a composite film.

Multiple casting aids may be placed within the container in random or ordered configurations. Accordingly, the sheets may be ordered in stacks or rolls in the containers. The container may contain, for example, a continuous web of material in compacted form having sheets connected in an end-to-end relationship separated by scored lines or perforations, from which the respective sheets can be readily dispensed, one at a time. Such a container may include a body containing the continuous web; a closure for the container; and a dispensing opening through which the web is withdrawn and a sheet of the web separated at the scored line or perforations. Preferably, as each sheet is pulled out and separated, the next sheet is exposed above the dispensing opening. The web may be in the form of a roll, and the web may be drawn for dispensing from the center of the roll. Alternatively, the sheets may be stacked face-to-face in the container. In yet another embodiment, the sheets may be partially overlapped or stacked as an interfolded array so that when one is withdrawn from the container, the next in the stack is presented in a graspable position.

Kits:

The present invention also provides kits for the formation of an orthopedic cast, comprising a casting material of this invention and a casting aid. The kits of this invention preferably comprise the casting aid and casting material in a suitable package. When the cast material is a thermoplastic, water-curable, or air-drying formulation, it is preferred for the casting material to be sealed in a compartment of the kit. The casting aid may be sealed in the same compartment as the casting material, or in a different compartment which may be sealed or unsealed. In a preferred embodiment, the casting material comprises a roll of sheets, around the circumference of which the casting aid is wrapped. Accordingly, such casting compositions of this invention comprise:

(a) a casting material formed into a roll; and
(b) a casting aid wrapped around the circumferences of said roll.

In another preferred embodiment, the casting aid and the casting tape are folded into a single roll, the roll being then sealed inside of a compartment of the kit. In yet a further embodiment of the invention, the casting aid and the casting tape are separated by a third layer, all three layers being folded into a single roll and the roll being then sealed inside of a compartment of the kit.

The sealing compartments may comprise a peelable layer over a shell of a material inert toward both the lubricant-impregnated substrate and the water-curable resin-impregnated cast sheet. Alternatively, the kit may comprise foil, foil-lined, plastic, or metallized plastic pouches or compartments.

The kit may further include gloves suitable for wearing during the cast molding process. Suitable gloves that may be used to handle the tacky material include gloves made from vinyl (such as polyvinyl chloride), latex, butyl rubber, or other such elastomeric materials. The gloves should be substantially nonporous to the lubricant so that the lubricant is not absorbed by the glove but instead remains, at least for the most part, on the surface of the glove.

The following non-limiting examples illustrate the compositions and methods of the present invention.

EXAMPLE 1

A casting material according to this invention is made comprising a casting tape of fiberglass with approximately 12% polypropylene fiber, about 7.6 cm (3 inches) wide and 3.7 m (4 yards) long and 1 mm (4 mil) thick. The tape has approximately 25% stretch and a mesh size at approximately 40.3 holes/cm$^2$ (260 holes/in$^2$). A 230-meter (250-yard) roll of casting tape is partially fused by applying a narrow band of heat at approximately 315° C. (600° F.), at 3.7-meter (4-yard) intervals. The roll is then dried at approximately 110° C. (230° F.) for approximately 4 hours.

A resin composition is made as having the following composition:

| Material | % (by weight) |
|---|---|
| Isonate ™ 2143L[1] | 30.8 |
| PPG 3025[2] | 64.4 |
| dimorpholinodiethyl ether | 3.9 |
| benzoyl chloride | 0.1 |
| silicone | 0.2 |
| butylated hydroxytoluene | 0.2 |
| titanium dioxide | 0.4 |

[1]modified diphenylmethane diisocyanate resin, assayed to contain 29.2% NCO, sold by Dow Chemical, Midland, Michigan
[2]a polypropylene glycol, having a molecular weight of approximately 3,000 and an assayed hydroxyl number of 38, sold by Lyondell Chemical Company, South Charleston, West Virginia
[3]35,000 centipoise polydimethylsiloxane, sold by Dow Corning Corp., Midland, Michigan The composition is made by admixture of the components, and heated with stirring to approximately 71° C. (160° F.) for approximately 4 hours. The roll of casting tape is removed from the drying oven and passed through the resin. After passing through the resin, the tape is squeezed through rollers to remove excess resin, so that the resin is impregnated at a level of about 42% by weight of the final impregnated tape. The tape is then cut where fused, to form individual strips of tape that are 3.7 m (4 yards) in length. An individual tape is then wound on a cylindrical core described in U.S. Pat. No. 5,984,884, Alvarez et al., issued Nov. 16, 1999 (incorporated by reference herein).

A casting aid is made having the following lubricating material composition.

| Material | % (by weight) |
|---|---|
| PVP K-90[4] | 64.0 |
| Aerosol OT-75%[5] | 3.3 |
| W610 Ceramic Zeeospheres[6] | 3.7 |
| water | 29.0 |

[4]solution containing approximately 20% polyvinylpyrrolidone in water, sold by BASF
[5]solution containing approximately 75% sodium dioctyl sulfosuccinate in ethanol/water, sold by Cytec Industries
[6]ceramic microspheres, sold by 3M The lubricating material is coated on a sheet of surface-oxidized Mylar® polyethylene film approximately 13 cm (5 inches) wide, 20 cm (8 inches) long, and 0.5 mm (2 mil) thick. The coated film is then dried in an oven, resulting in a coating layer approximately 0.34 mm (1.5 mils) thick. The casting aid is then wrapped around the roll of impregnated casting sheet. The wrapped roll is sealed in a foil pouch under nitrogen, along with a desiccant pouch, to make a kit according to this invention.

The sealed pouch is later opened and the orthopedic casting article is removed. Using latex gloves, the roll of casting material covered with the casting aid is placed in water and squeezed twice while underwater. The roll is then taken out of the water and squeezed to remove excess amounts of water. The covered roll is used to wet both gloves being worn by rolling it between the palm and wiping both palm, transferring lubricating material from the casting aid to the gloves. The casting aid is then laid aside and the wrapping process begun.

The casting sheet is next unrolled while wrapping the sheet around the limb of a human subject to form a cast. The lubricated gloves prevent the resin from the tape from sticking to the gloves and allow the hands to move freely in the molding of the cast. The casting aid is used to re-apply more lubricant to coat the palms of the gloves during the wrapping process.

In the above Example, the free NCO level is determined to be 7.5%, as follows.

$$\# \text{ eq NCO} = A\% \times B \text{ grams} \div 42.02 \text{ grams/equivalent}^7$$
$$= (0.292)30.8 \text{ g} \div 42.02 \text{ g/eq} = 0.214 \text{ eq}$$
$$\# \text{ eq OH} = C\% \times D \text{ grams} \div 56.1 \text{ grams/equivalent}^8$$
$$= 0.038 \times 64.4 \text{ g} \div 56.1 \text{ g/eq} = 0.043 \text{ eq}$$
$$\# \text{ eq free NCO} = \# \text{ eq NCO} - \# \text{ eq OH}$$
$$= 0.214 - 0.043 = 0.071$$
$$\text{free NCO level} = \# \text{ eq free NCO} \times 42.02 \text{ grams/eq}^4 \div$$
$$(B \text{ grams} + D \text{ grams})$$
$$= 0.171 \text{ eq} \times 42.02 \text{ g/eq} \div (30.8 + 64.4) \text{ g}$$
$$= 0.075 = 7.5\%$$

wherein, $A$ = assayed % NCO in isocyanate $B$ = weight of isocyanate (per 100 grams of resin)

$C$ = assayed hydroxyl number for polyol
  (mg KOH equivalents per gram polyol)

$D$ = weight of polyol (per 100 grams of resin)

[7]equivalent weight of NCO

[8]equivalent weight of KOH

The examples and other embodiments described herein are exemplary and not intended to be limiting in describing the full scope of compositions and methods of this invention. Equivalent changes, modifications and variations of specific embodiments, materials, compositions and methods may be made with substantially similar results.

EXAMPLE 2

A casting material is made comprising a casting tape of fiberglass with approximately 10% polypropylene fiber, about 10.2 cm (4 inches) wide and 3.7 m (4 yards) long and 1 mm (4 mil) thick. The tape has approximately 25% stretch and a mesh size at approximately 43.4 holes/cm$^2$ (280 holes/in$^2$). The tape is impregnated with a resin composition having the following composition:

| Material | % (by weight) |
| --- | --- |
| diphenylmethane diisocyanate[9] | 35.6 |
| polypropylene glycol ether[10] | 59.4 |
| 4-[2-[methyl-2-(4-morpholinyl) ethoxy]-ethyl]morpholine | 4.1 |
| benzoyl chloride | 0.1 |
| silicone | 0.1 |
| butylated hydroxytoluene | 0.3 |
| titanium dioxide | 0.4 |

[9]assayed to contain 29.0% NCO
[10]a polypropylene glycol, having a molecular weight of approximately 3,500 and an assayed hydroxyl number of 40

The tape is impreganted with the resin according to the method described in Example 1. The free NCO level is calculated to be 9%, using the method described in Example 1.

What is claimed is:

1. An orthopedic casting material comprising a substrate impregnated with a water-curable prepolymer comprising an aromatic polyisocyanate and a polyol, wherein the free NCO level of said prepolymer is from about 6% to 10%, wherein said casting material is substantially free of lubricating materials.

2. An orthopedic casting material according to claim 1, wherein said free NCO level is from about 7% to about 8%.

3. An orthopedic casting material according to claim 2, wherein said polyol is a polyalkylene ether.

4. An orthopedic casting material according to claim 2, wherein said polyol has a hydroxyl number of from about 28 to about 56.

5. An orthopedic casting material according to claim 4, wherein said polyol has a hydroxyl number of from about 28 to about 46.

6. An orthopedic casting material according to claim 5, wherein said polyol has a hydroxyl number of from about 35 to about 40.

7. An orthopedic casting material according to claim 6, wherein said free NCO level is about 7.5%.

8. An orthopedic casting material according to claim 1, wherein said free NCO level is from about 6% to about 7.5%.

9. An orthopedic casting material according to claim 8, wherein said free NCO level is from about 7% to about 7.5%.

10. An orthopedic casting material according to claim 1, wherein said isocyanate comprises diphenylmethane diisocyanate.

11. An orthopedic casting material according to claim 1, wherein said substrate is a flexible sheet comprising fibers selected from the group consisting of fiberglass, polyalkylene, polyaramide, polyester, acrylonitrile copolymer fibers, and mixtures thereof.

12. An orthopedic casting material according to claim 11, wherein said flexible sheet comprises a mixture of fiberglass and polypropylene fibers.

13. A method of forming an orthopedic cast by hand around a body member of a human or other animal subject using an orthopedic casting material according to claim 1.

14. A method of forming an orthopedic cast by hand around a body member of a human or other animal subject, using:
  (a) a casting material according to claim 1;
  (b) a casting aid, comprising a substrate and a lubricating material coated on said substrate; and
  (c) a glove, comprising the steps of:
(1) transferring said lubricating material to a surface of said glove;
(2) applying said casting material to said body member using said glove; and
(3) allowing said casting material to harden to form said orthopedic cast.

15. A kit for the formation of an orthopedic cast, comprising:
(a) a casting material according to claim 1; and
(b) a casting aid comprising a substrate and a lubricating material coated on said substrate.

16. An orthopedic casting material comprising a substrate impregnated with a water-curable prepolymer comprising an aromatic polyisocyanate and a polyol, wherein the free NCO level of said prepolymer is from about 6% to about 7.5%.

17. An orthopedic casting material according to claim 16, wherein said free NCO level is from about 7% to about 7.5%.

18. An orthopedic casting material according to claim 16, wherein said prepolymer is substantially free of a lubricant.

19. An orthopedic casting material according to claim 16, wherein said isocyanate comprises diphenylmethane diisocyanate.

20. An orthopedic casting material according to claim 16, wherein said polyol is a polyalkylene ether.

21. An orthopedic casting material according to claim 16, wherein said polyol has a hydroxyl number of from about 28 to about 56.

22. An orthopedic casting material according to claim 21, wherein said polyol has a hydroxyl number of from about 28 to about 46.

23. An orthopedic casting material according to claim 22, wherein said polyol has a hydroxyl number of from about 35 to about 40.

24. An orthopedic casting material according to claim 23, wherein said free NCO level is about 7.5%.

25. An orthopedic casting material according to claim 16, wherein said substrate is a flexible sheet comprising fibers selected from the group consisting of fiberglass, polyalkylene, polyaramide, polyester, acrylonitrile copolymer fibers, and mixtures thereof.

26. An orthopedic casting material according to claim 25, wherein said flexible sheet comprises a mixture of fiberglass and polypropylene fibers.

27. A method of forming an orthopedic cast by hand around a body member of a human or other animal subject using an orthopedic casting material according to claim 16.

28. A method of forming an orthopedic cast by hand around a body member of a human or other animal subject, using:
(a) a casting material according to claim 16;
(b) a casting aid, comprising a substrate and a lubricating material coated on said substrate; and
(c) a glove, comprising the steps of:
(1) transferring said lubricating material to a surface of said glove;
(2) applying said casting material to said body member using said glove; and
(3) allowing said casting material to harden to form said orthopedic cast.

29. A kit for the formation of an orthopedic cast, comprising:
(a) a casting material according to claim 16; and
(b) a casting aid comprising a substrate and a lubricating material coated on said substrate.

30. A kit for the formation of an orthopedic cast, comprising:
(a) a casting material comprising a substrate impregnated with a water-curable prepolymer comprising aromatic polyisocyanate and a polyol, wherein the free NCO level of said prepolymer is from about 6% to 10%; and
(b) a casting aid comprising a substrate and a lubricating material coated on said substrate.

31. An orthopedic casting material according to claim 30, wherein said free NCO level is from about 7% to about 8%.

32. An orthopedic casting material according to claim 30, wherein said free NCO level is from about 6% to about 7.5%.

33. An orthopedic casting material according to claim 32, wherein said free NCO level is from about 7% to about 7.5%.

34. An orthopedic casting material according to claim 30, wherein said prepolymer is substantially free of a lubricant.

35. An orthopedic casting material according to claim 30, wherein said isocyanate comprises diphenylmethane diisocyanate.

36. An orthopedic casting material according to claim 30, wherein said polyol is a polyalkylene ether.

37. An orthopedic casting material according to claim 30, wherein said polyol has a hydroxyl number of from about 28 to about 56.

38. An orthopedic casting material according to claim 37, wherein said polyol has a hydroxyl number of from about 28 to about 46.

39. An orthopedic casting material according to claim 38, wherein said polyol has a hydroxyl number of from about 35 to about 40.

40. An orthopedic casting material according to claim 39, wherein said free NCO level is about 7.5%.

41. An orthopedic casting material according to claim 30, wherein said substrate is a flexible sheet comprising fibers selected from the group consisting of fiberglass, polyalkylene, polyamide, polyester, acrylonitrite copolymer fibers, and mixtures thereof.

42. An orthopedic casting material according to claim 41, wherein said flexible sheet comprises a mixture of fiberglass and polypropylene fibers.

* * * * *

UNITED STATES PATENT AND TRADEMARK OFFICE
CERTIFICATE OF CORRECTION

PATENT NO. : 6,673,727 B2
DATED : January 6, 2004
INVENTOR(S) : Roy A. Morris

It is certified that error appears in the above-identified patent and that said Letters Patent is hereby corrected as shown below:

<u>Title page</u>,
Item [75], Inventors, add -- Eric R. Jania, Rockaway, NJ --

<u>Column 1</u>,
Line 46, delete "issued Feb. 28, 1984;"

<u>Column 2</u>,
Line 67, "MDI's" should be -- MDIs --

<u>Column 4</u>,
Line 23, delete 1$^{st}$ occurrence of "is"

<u>Column 5</u>,
Line 66, "commercially product" should be -- product commercially --

<u>Column 7</u>,
Line 40, "Paten" should be -- Patent --

<u>Column 11</u>,
Lines 9 and 10, "palm" should be -- palms --
Line 32, "0.071" should be -- 0.171 --

Signed and Sealed this

Thirty-first Day of August, 2004

JON W. DUDAS
*Director of the United States Patent and Trademark Office*